United States Patent [19]

Spino et al.

[11] 4,107,843
[45] Aug. 22, 1978

[54] ORTHODONTIC APPLIANCE

[76] Inventors: Raymond N. Spino, 264 W. Valley Brook Rd.; Casimir G. Warren, P.O. Box 94, both of Califon, N.J. 07830

[21] Appl. No.: 726,124

[22] Filed: Sep. 24, 1976

[51] Int. Cl.² ............................................. A61C 7/00
[52] U.S. Cl. .................................................... 32/14 E
[58] Field of Search .................. 34/14 A, 14 C, 14 D, 34/14 E

[56] References Cited
U.S. PATENT DOCUMENTS 3,284,902  11/1966  Dillberg et al. ............... 32/14 E

*Primary Examiner*—Robert Peshock
*Attorney, Agent, or Firm*—Carella, Bain, Gilfillan & Rhodes

[57] ABSTRACT

Biasing apparatus for use as a component of an orthodontic appliance is disclosed to include opposed telescoping elements which are positively biased by a telescoping threaded operating means, wherein the operating means is substantially totally encased within the outer telescoping casing.

14 Claims, 5 Drawing Figures

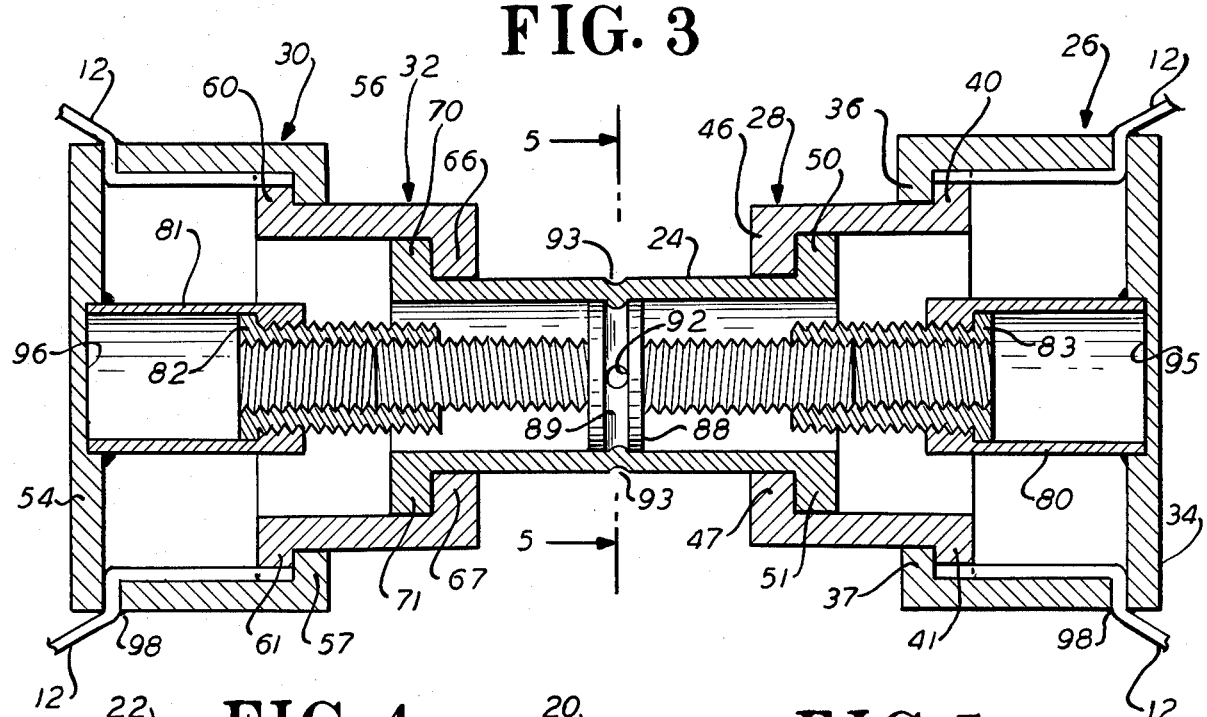
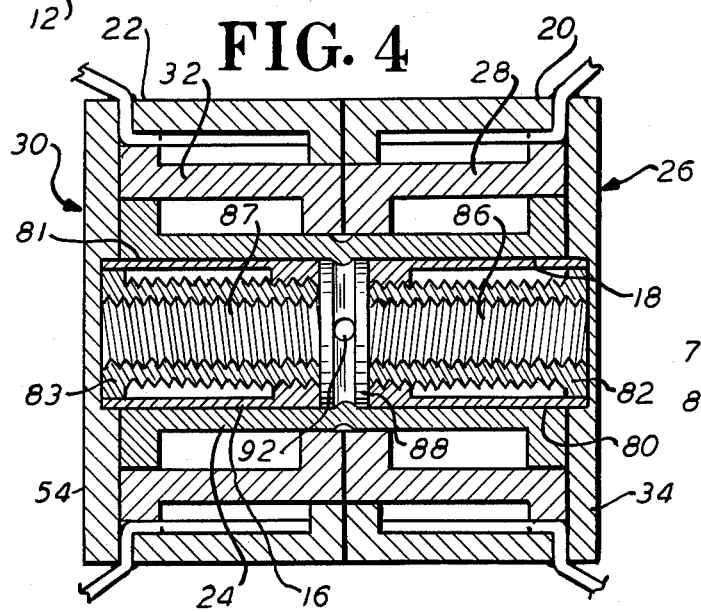
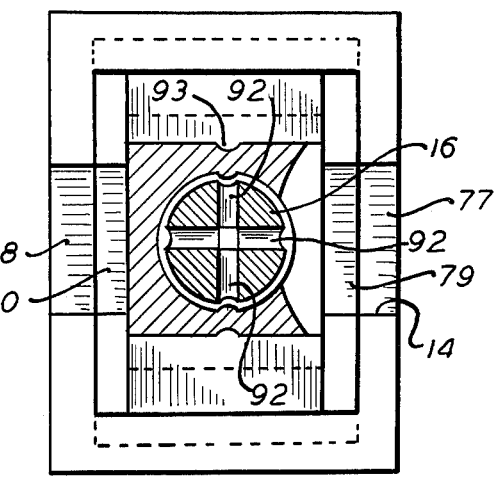
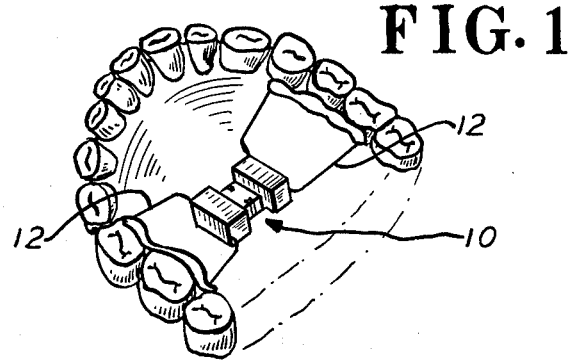

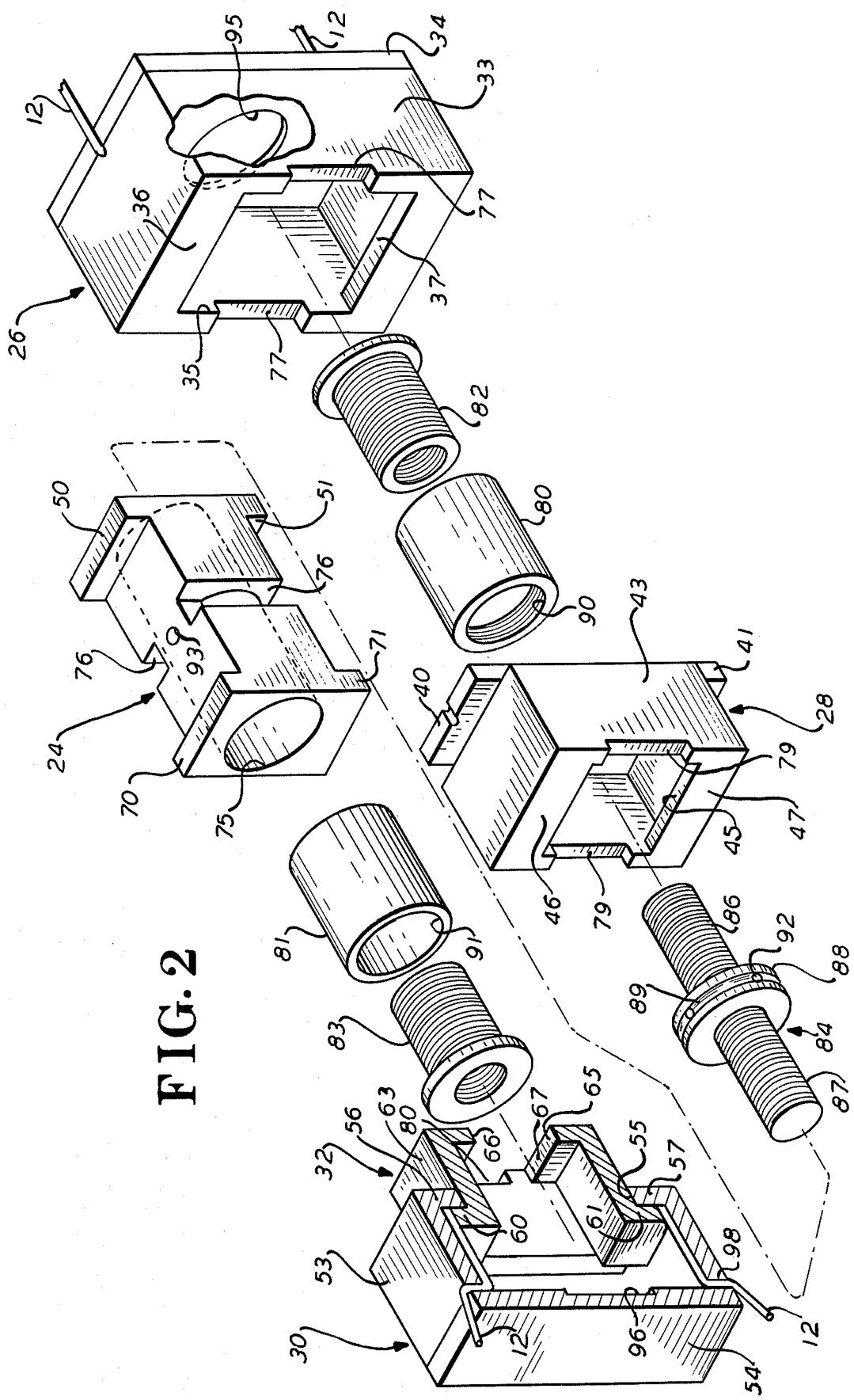

ORTHODONTIC APPLIANCE

BACKGROUND OF THE INVENTION

This invention relates to the field of orthodontic appliances. More specifically, this invention relates to biasing apparatus for orthodontic appliances of the type used to effect palate widening.

As will be recognized by those skilled in these arts, it is often desirable or necessary for an orthodontist to cause a widening of the upper arch of patient's mouth. Such widening may be desirable in order to develop sufficient room for teeth to fit into place, to align upper teeth with lower teeth or to correct for high palate and narrow arch, e.g. to improve breathing. For whatever the reason, such palate widening has been achieved for the most part by cementing an appliance between the teeth of a patient and gradually expanding the appliance to generate an outwardly directed bias.

Typical examples of known biasing devices are disclosed in U.S. Pat. Nos. 360,695; 3,284,902 and 3,832,778. Such known appliances, as well as others, suffer from various disadvantages which render them undesirable from an orthodontic point of view as well as from the point of view of the patient.

From the orthodontist's point of view, known biasing devices are undesirable because it is required that a plurality of sizes be kept in stock. Thus, it is generally recognized in the field that orthodontic appliances having three basic sizes should be stocked in order to provide the range of expansion necessary for accommodating different sized mouths. Thus, a stock investment of significant proportion may be required either by the orthodontist or by the dental technician serving the orthodontist.

Further, in those cases wherein a large degree of expansion is required, it is a presently acceptable technique to commence pallate expansion with a small appliance and thereafter substitute a larger appliance in order to complete the amount of expansion required. This of course requires additional visits to the orthodontist's office and subject the patient to undesirable additional discomfort.

A still further disadvantage from the orthodontists' point of view is that known apparatus are subject to reduction in bias by the patient. Specifically, with exposed operating threads there has occurred a backing-off of the threaded biasing members as a result of accidental manipulation by the patient. In known devices, once a desired expansion has been achieved, such backing off has been precluded by wiring the apparatus in place. Such wiring is not required by the present invention.

From the patient's point of view the known style orthodontic appliances create two particular problems, irritation and food retention.

As is clear from reference to the above-identified patents which are submitted to be typical of the prior art, there occurs in known orthodontic biasing appliances the exposure of the patient's tongue to the threaded surfaces of the operating device. Exposure of the tongue to such threaded surfaces invariably causes irritation, discomfort and, on occasion, laceration. Any such injury or discomfort is highly undesirable from the patient's point of view and a source of continuing difficulty for the orthodontist. In addition to the question of discomfort resulting from exposed screw threads attendant to the device, there is also the unhealthy and also discomforting tendency of known orthodontic biasing devices to retain food particles. Thus, the food may well become lodged in the operating mechanism of the known devices or it may become lodged partially in the operating mechanism and partially between the mechanism and the pallate of the user. It is evident that food so lodged is extremely difficult to remove and extremely undesirable from all standpoints.

SUMMARY OF THE INVENTION

It is an object of the present invention, therefore, to provide an orthodontic biasing apparatus wherein only one biasing apparatus is required to achieve degrees of expansion which range from the smallest width ordinarily required to the largest width ordinarily required through the use of but a single apparatus.

An additional object of the invention is to provide an orthodontic biasing apparatus which is smaller than comparable apparatuses generally presently available.

A still further object of the present invention is to provide an orthodontic biasing apparatus wherein the operating mechanism is isolated from the tongue of the patient so as to avoid the occurence of injury of discomfort heretofore known.

Yet another object of the present invention is to provide an orthodontic biasing apparatus wherein isolation of the operating mechanism as well as the overall structure of the apparatus preclude the possibility that food may be lodged or retained in the operating mechanism thus avoiding hygenic difficulties attendant to trapped foods.

Yet another advantage of orthodontic biasing apparatus according to the present invention is that the structure precludes disassembly in place thus obviating the necessity for the use of stabilizing wires of the type generally known in these arts. Further, because the operating apparatus is encased within the outer structure casing, there is less tendency for reversal of the expansion process by manipulation of the operating screws with the tongue.

Finally, it is an object of the present invention to provide an orthodontic biasing apparatus wherein the operating mechanism is protected against damage by deflection and the like e.g. of the type which occurs when a patient accidentally bites on a piece of bone or on something hard such as is particularly a danger when the appliance is being used with children.

These objects and others are achieved by the biasing apparatus according to the present invention, one embodiment of which may include a first telescoping element; a second telescoping element; a central section having a first and a second end, the first end of the central section being slidably received within the first telescoping element and a second end of the central section being slidably received within the second telescoping element, and wherein there is provided operating means mounted within a cavity defined by the first and second telescoping elements and the central section, the operating means being for causing displacement of the first and second telescoping elements between an extended position and a retracted position, and wherein the operating means is made accessible through an access means formed in the first and second telescoping elements and the central section.

BRIEF DESCRIPTION OF DRAWINGS

A more complete understanding of the present invention may be had from the following detailed description thereof, particularly when read in the light of the accompanying drawings wherein:

FIG. 1 is a perspective view of a biasing apparatus according to the invention positioned in a patient's mouth and connected to the patient's teeth;

FIG. 2 is a partial cross-sectional exploded view of the biasing apparatus according to the invention;

FIG. 3 is a cross sectional elevational view of the biasing apparatus of the present invention shown in an expanded position;

FIG. 4 is a cross sectional elevational view of biasing apparatus according to the invention shown in a retracted position; and FIG. 5 is a cross sectional view of biasing apparatus according to the invention as seen through plane 5—5 of FIG. 3.

DETAILED DESCRIPTION

Referring therefore to FIG. 1, an orthodontic biasing apparatus structured in accordance with the teaching of the present invention is shown and designated generally by the reference numeral 10. Biasing apparatus 10 is rigidly connected to the teeth of a patient by palate bars 12. As will be recognized by those skilled in these arts, palate bars 12 may be welded or soldered to the biasing apparatus 10 pursuant to the needs of the situation.

Biasing apparatus 10 is a device manufactured for the most part from surgical grade stainless steel. As is discussed below in detail it comprises a telescoping structure which may be adjusted to create a biasing face against the teeth of the user. More specifically, apparatus 10 is expansible in response to operation of the device by insertion of a tool (not shown) through an access means 14 formed in the apparatus and rotation of an expansible operating means 16 contained within a cavity 18 in apparatus 10.

Considering therefore the detailed structure of apparatus 10 and with particular reference to FIGS. 2 through 4, the apparatus can be seen to include an outer casing having a first telescoping element 20 and a second telescoping element 22, each of which is slidably received over a central casing section 24.

First telescoping element 20 comprises an end section 26 and an intermediate section 28. Similarly, second telescoping element 22 comprises an end section 30 and an intermediate section 32.

End section 26 comprises a generally rectangular member 33 having a wall 34 closing one end and a generally rectangular opening 35 formed in the other outer end. Rectangular opening 35 is defined by the vertical walls of the rectangular body 33 and upper and lower flanges 36,37 which extend normally inwardly from the upper and lower horizontal walls of body 33. Flanges 36, 37 cooperate with outwardly extending flanges 40, 41 formed on one end of intermediate section 28 to limit the degree of telescoping extension between first end section 26 and intermediate section 28.

Intermediate section 28 comprises a generally rectangular body 43 having a generally rectangular opening formed to extend longitudinally therethrough. The cross-sectional configuration of rectangular body 43 corresponds dimensionally to the cross-sectional configuration of rectangular opening 35 such as to be slidably received therethrough. The end of body 43 adjacent flanges 40, 41 is open to accommodate the passage therethrough of an operating means as is discussed below in detail. The opposite or inwardly positioned end of body 43 is provided with a generally rectangular opening 45. Rectangular opening 45 is defined by the vertical walls of the rectangular body 43 and upper and lower flanges 46,47 which extend normally inwardly from the upper and lower horizontal walls of body 43. Flanges 46,47 cooperate with outwardly extending flanges 50,51 formed on one end of central section 24 to limit the degree of telescoping extension between intermediate section 28 and central section 24.

Second telescoping element 22 is identical in structure to first telescoping element 20 but opposite hand as shown. Thus end section 30 of second telescoping element 22 comprises a generally rectangular body member 53 having a wall 54 closing one end and a generally rectangular opening 55 formed in the other end. Rectangular opening 55 is defined by the vertical walls of body 53 and upper and lower flanges 56,57 which extend normally inwardly from the upper and lower horizontal walls of body 53. Flanges 56,57 cooperate with outwardly extending flanges 60,61 formed on one end of intermediate section 32 to limit the degree of telescoping extension between first end section 30 and intermediate section 32.

Intermediate section 32 comprises a generally rectangular body 63 having a generally rectangular opening formed to extend longitudinally therethrough. The cross-sectional configuration of rectangular body 63 corresponds dimensionally to cross-sectional configuration of rectangular opening 55 such as to be slidably received therethrough. The end of body 63 adjacent flanges 60,61 is open to accommodate the passage therethrough of an operating means as is discussed below in detail. The opposite or inwardly positioned end of body 63 is provided with a generally rectangular opening 65. Rectangular opening 65 is defined by the vertical walls of body 63 and upper and lower flanges 66, 67 which extend normally inwardly from the upper and lower horizontal walls of body 63. Flanges 66 and 67 cooperate with outwardly extending flanges 70,71 formed on the end of central section 24 longitudinally opposite the one end on which flanges 50,51 are formed, to limit the degree of telescoping expansion between intermediate section 32 and central section 24.

Central section 24 is a generally rectangular element having a longitudinally extending bore 75 formed therethrough and flanges 50,51,70 and 71 formed thereon as aforesaid. Formed longitudinally centrally of central section 24 and extending transversely through a portion of the wall thereof are opposed slots 76 which cooperates with relieved portions 77,78, 79 and 80 formed in the inner end edge surfaces of the vertical walls of end sections 26,30 and intermediate sections 28, 32 to define access means 14 for permitting operation of apparatus 10 as discussed below.

The hollow interiors of first and second telescoping elements 20 & 22 cooperate to define cavity 18 in which operating means 16 is housed.

The operating means 16 comprises five elements: first and second end operating elements 80, 81, first and second intermediate operating elements 82, 83 and central operating element 84.

Central operating element 84 comprises a generally cylindrical member having a first end portion 86, a second end portion 87 and a centrally disposed radially extending hub 88. In this regard it should be noted that hub 88 has a plurality of radially extending through bores 92 formed therein, the bores being for the accommodation of an operating tool as is discussed below in detail with respect to the use of apparatus 10. Hub 88 is also circumferentially relieved to define an annular channel 89. Channel 89 cooperates with opposed dimples 93 formed on central section 24 to preclude longitudinally axial movement of central operating element 84 within central section 24 during adjustment. The interior surfaces of first and second ends 80, 81 of central operating section are threaded with opposite hand threads.

Intermediate operating sections 82 and 83 are generally cylindrical members which are threaded on their external surfaces and tapped on their internal surfaces. The inner dimension of the intermediate members and the particular tap dimension is chosen to permit the intermediate members to be threadedly engaged on the threaded surfaces of first and second ends 86 and 87 of the central operating number 84.

The threaded outer surfaces of intermediate operating elements 82 and 83 are structured to be threadedly received within tapped openings formed in outer operating members 80, 81, respectively.

In this regard outer operating members are generally cylindrical elements having a longitudinally axially extending bore 90, 91 formed therethrough. One end of each end element is rigidly secured e.g. by welding or soldering, within a circularly shaped relieved portion 95, 96 formed in the end walls of the first and second end sections of telescoping elements 20, 22, respectively. Disposed on the end of end section 80 and 81 is a radially inwardly extending shoulder having a tapped bore therethrough. Tapped bore is dimensioned to threadedly receive the threads of the outer surface of intermediate sections 82 and 83.

As also may best be seen in FIG. 2 the upper and lower walls of end sections 26 and 30 are provided with bores 98 through which extend palate bars 12. Bars 12 are bent to be in surface-to-surface engagement with the inner surfaces of the end sections. Further, flags 40, 41 and 60, 61 of intermediate sections 28, 32 are relieved to provide clearance for the sliding of the intermediate section over the palate bars during operation.

Thus it can be seen that the operating means of apparatus 10 comprises telescopically extending threaded sections which are threaded using opposite end threads such as to permit threaded expansion or retraction of the operating means in response to rotation of the central operating section in either a clockwise or counterclockwise direction.

In using apparatus 10 according to the invention, the apparatus is mounted within the mouth of the patient and secured to the teeth of the patient by palate bars and bans in a manner generally known in the art. In this regard the palate bars are secured to apparatus 10 prior to insertion of the apparatus in the mouth of the patient. Further it will be recognized that the palate bars may be rigidly secured to apparatus 10 by welding, soldering or the like either to the external surfaces of apparatus 10 of within the cavity of apparatus 10 in the manner shown in the event that it is decided to pass the ends of the palate bars into the apparatus cavity. With the palate bars positioned within the appartus cavity they may be tack welded to the surface of end section 26 and 30.

The apparatus is installed in the patient's mouth in the retracted position where it is desired to effect a widening of the palate. With the apparatus so emplaced the apparatus is regularly telescopically extended by rotation of the hub on central operating section 84. This is effected by inserting a rigid but wirelike tool in one of the radial through bars 92 formed in the central hub 88 of central section 84 and rotating by a desired amount. In this regard it will be recognized by those skilled in these arts that radially extending throughbars 92 should be positioned such that rotation of the hub by a sufficient arcuate amount to effect a desired adjustment in telescopic positioning of the apparatus will cause the next adjacent radially extending opening to appear in access slot 14. It should be noted that throughbars 92 are so structured to permit through insertion of the rotating tool to also clean any food or other debris which may accumulate therein.

As will be recognized from the foregoing detailed description of the invention, none of the threaded portions of the operating means are exposed to the mouth of the patient. Rather they are all contained within the cavity defined by the hollow casing of the apparatus. This of course isolates the potentially abrasive threaded portions from the tongue of the patient thus reducing the likelihood of irritation. The substantially totally enclosed structure of the apparatus also reduces the incidence of food retention in the appliance which often is not only unpleasant but also unsanitary.

It is further submitted to be clear that the structure of the present invention, by reason of its positive control telescoping operation does not rely on retaining wires to maintain position within the mouth of the patient and as such is less complex when retention at the position of desired expansion is necessary. Further, the telescoping structure of the apparatus as shown permits the degree of adjustment in a single appliance which heretofore has been impossible.

Accordingly it is respectfully submitted that the apparatus according to the invention defines a significant improvement and step forward both in structure and operation in the orthodontics appliance art.

It will further be recognized by those skilled in these arts that modifications and variations to the structure or operation of the present apparatus may be made without departing from the spirit and scope of this teaching.

What is claimed is:

1. Biasing apparatus for use as a component of an orthodontic appliance, comprising:
   (a) a first telescoping element;
   (b) a second telescoping element;
   (c) a central section having a first end and a second end, the first end of said central section being slidably received within said first telescoping element and the second end of said central section being slidably received within said second telescoping element;
   (d) said first and second telescoping elements and said central section cooperating to define a cavity;
   (e) operating means disposed within said cavity for causing displacement of said first and second telescoping elements between an extended position and a retracted position, said operating means being in threaded engagement with said first and second telescoping elements and in rotating sliding engagement with said central section; and
   (f) access means formed in said first and second telescoping elements and said central section to provide access for an operator to said operating means.

2. Biasing apparatus for use as a component of an orthodontic appliance, comprising:
   (a) a first telescoping element, said first telescoping element comprising an end section and at least one intermediate section;

(b) a second telescoping element, said second telescoping element comprising an end section and at least one intermediate section;

(c) a central section having a first end and a second end, the first end of said central section being slidably received within said first telescoping element and the second end of said central section being slidably received within said second telescoping element;

(d) said first and second telescoping elements and said central section cooperating to define a cavity;

(e) operating means disposed within said cavity for causing displacement of said first and second telescoping elements between an extended position and a retracted position; and (f) access means formed in said first and second telescoping elements and said central section to provide access for an operator to said operating means.

3. Apparatus according to claim 2 wherein said end sections of said first and second telescoping elements are slidably received around said intermediate sections of said first and second telescoping elements, respectively, and said first and second intermediate sections are slidably received around said central section.

4. Apparatus according to claim 2 wherein said end sections of said first and second telescoping elements are in abutting engagement when said apparatus is in said retracted position.

5. Apparatus according to claim 2 wherein said operating means includes a first end and a second end and wherein said first end is rigidly secured to said first end section and said second end is rigidly secured to said second end section.

6. Apparatus according to claim 2 wherein said first telescoping operating element comprises an end operating section and at least one intermediate operating section and further wherein said second telescoping operating element comprises an end operating section and at least one intermediate operating section.

7. Apparatus according to claim 6 wherein said end operating sections of said first and second telescoping operating elements are generally cylindrical and provided with bores extending therethrough, at least a portion of said bores being tapped; and wherein each said intermediate operating sections is generally cylindrical having a threaded outer surface for being threadedly received within said threaded bores of said end sections, and a tapped inner surface for threadedly receiving therein the threaded outer surface of said central operating section.

8. Apparatus according to claim 7 wherein said end operating section of said first telescoping operating element is rigidly secured to said first telescoping element and said end operating section of said second telescoping operating element is rigidly secured to said second telescoping element.

9. Biasing apparatus for use as a component of an orthodontic appliance, comprising:

(a) a first telescoping element, said first telescoping element including an end section and at least one intermediate section telescopically received therein;

(b) a second telescoping element, said second telescoping element including an end section and at least one intermediate section telescopically received therein;

(c) a central section having a first end and a second end, said first end of said central section being telescopically slidably received within said first telescoping element and said second end of central section being telescopically slidably received within said second telescoping element;

(d) a cavity formed by the cooperation of said first telescoping element, said second telescoping element and said central section;

(e) operating means disposed within said cavity for causing displacement of said first and second telescoping elements between an extended position and a retracted position; and (f) access means in said first and second telescoping elements and said central section to provide access for an operator to said operating means.

10. Biasing apparatus according to claim 9 wherein said operating means includes a first end operating section and a second end operating section and wherein said first end operating section is rigidly secured to said first end section of said first telescoping element and said second end operating section is rigidly secured to said second end section of said second telescoping element.

11. Biasing apparatus according to claim 10 wherein said operating means includes a central operating section and at least one intermediate operating section.

12. Biasing apparatus according to claim 11 including a total receiving means disposed on said central operating section, said tool receiving means being aligned with said access means such as to permit an operator to gain access to said tool receiving means to operate said apparatus between extended and retracted positions.

13. Biasing apparatus according to claim 12 wherein said tool receiving means comprises a hub disposed on said central operating section having arcuately spaced radially extending bores therein.

14. Biasing apparatus according to claim 12 including an annular channel formed in the circumferential surface of said hub and dimples formed in the surface of said central section, said dimples being slidably received within said annular channel to preclude non-rotational movement of said central operating section.

* * * * *